US009770168B2

United States Patent
Pohjanen et al.

(10) Patent No.: US 9,770,168 B2
(45) Date of Patent: Sep. 26, 2017

(54) DEVICE FOR IMAGING AN EYE (71) Applicant: Trividi Oy, Oulu (FI)

(72) Inventors: Petri Pohjanen, Oulu (FI); Nora Kaarela, Helsinki (FI); Jukka Alasirnio, Jaali (FI)

(73) Assignee: Trividi Oy, Oulu (FI)

( * ) Notice: Subject to any disclaimer, the term of this patent is extended or adjusted under 35 U.S.C. 154(b) by 243 days.

(21) Appl. No.: 14/424,265

(22) PCT Filed: Sep. 12, 2013

(86) PCT No.: PCT/FI2013/050880
§ 371 (c)(1),
(2) Date: Feb. 26, 2015

(87) PCT Pub. No.: WO2014/041247
PCT Pub. Date: Mar. 20, 2014

(65) Prior Publication Data
US 2015/0208918 A1   Jul. 30, 2015

(30) Foreign Application Priority Data

Sep. 12, 2012 (FI) .................................... 20125945
Jan. 16, 2013 (FI) .................................... 20135047

(51) Int. Cl.
*A61B 3/14* (2006.01)
*A61B 3/113* (2006.01)
(Continued)

(52) U.S. Cl.
CPC .............. *A61B 3/14* (2013.01); *A61B 3/0008* (2013.01); *A61B 3/0025* (2013.01);
(Continued)

(58) Field of Classification Search
CPC ......... A61B 3/0091; A61B 3/113; A61B 3/12; A61B 3/1208; A61B 3/14; A61B 3/145
(Continued)

(56) References Cited

U.S. PATENT DOCUMENTS 5,943,116 A   8/1999   Zeimer
6,296,358 B1  10/2001  Cornsweet et al.
(Continued)

FOREIGN PATENT DOCUMENTS

CN   1468581   1/2004
CN   1951314   4/2007
(Continued)

OTHER PUBLICATIONS

International Search Report for FI20125945 dated May 7, 2013.
(Continued)

*Primary Examiner* — Huy K Mai
(74) *Attorney, Agent, or Firm* — Andrus Intellectual Property Law, LLP (57) ABSTRACT

A device is for imaging an eye and is wearable on the object to be examined or otherwise able to be placed to the front of an eye or eyes. When the device is switched on, it automatically performs the imaging such that all images are useful. The device comprises a camera arrangement with optics and a camera sensor, and an illumination arrangement. The device comprises a control arrangement that switches the camera arrangement to take automatically one or more images of the eye, when the device is in front of the eye. The device comprises an image analyzing arrangement or a connection to an image analyzing arrangement that is provided for detecting a reflection in the image taken by the camera arrangement or in the image area of the camera arrangement and for transmitting the information about the detected reflection to the control arrangement which is
(Continued)

provided thereby to repeat or decline imaging. When repeating the imaging the control arrangement alters the parameters of imaging.

20 Claims, 6 Drawing Sheets (51) Int. Cl.
*A61B 3/12* (2006.01)
*A61B 3/00* (2006.01)
*A61B 3/15* (2006.01)
(52) U.S. Cl.
CPC ............ *A61B 3/0091* (2013.01); *A61B 3/113* (2013.01); *A61B 3/12* (2013.01); *A61B 3/156* (2013.01)
(58) Field of Classification Search
USPC .................. 351/205, 206, 209, 210, 211, 212
See application file for complete search history.

(56) References Cited

U.S. PATENT DOCUMENTS 6,411,839 B1 6/2002 Okinishi
2003/0231242 A1 12/2003 Matsumoto
2007/0030450 A1 2/2007 Liang et al.
2010/0220291 A1* 9/2010 Horning ............... G02B 27/017
351/210
2011/0051087 A1 3/2011 Inoue et al.

FOREIGN PATENT DOCUMENTS

| CN | 102379681 | 3/2012 |
| JP | H105195 | 1/1998 |
| JP | 3337913 B2 | 10/2002 |
| JP | 2011224213 | 11/2011 |
| WO | 01/28411 | 4/2001 |
| WO | 2010051304 A1 | 5/2010 |

OTHER PUBLICATIONS

International Search Report for PCT/FI2013/050880 dated Dec. 2, 2013.
The First Office Action, Chinese Patent Application No. 201380057539.4, issuing date Mar. 23, 2016, with English translation.
EPO Search Report, EP Patent Application No. 13837252.9, date of mailing Jun. 7, 2016.

* cited by examiner

DEVICE FOR IMAGING AN EYE

CROSS-REFERENCE TO RELATED APPLICATIONS

This application is the U.S. national stage application of International Application PCT/FI2013/050880, filed Sep. 12, 2013, which international application was published on Mar. 20, 2014, as International Publication WO2014/041247 in the English language. The international application is incorporated herein by reference, in entirety. The international application claims priority to Finnish Patent Application No. 20125945, filed Sep. 12, 2012, and Finnish Patent Application No. 20135047, filed on Jan. 16, 2013, which are incorporated herein by reference, in entirety.

The invention relates to a device that is provided for examining an eye or eyes of an object, the device comprising one or more camera arrangements, the camera arrangement comprising optics and a camera sensor, the camera arrangement being provided to image the fundus or the surface of an eye or both, and one or more illumination arrangements.

PRIOR ART

Eyes and especially fundi are imaged in order to detect different diseases or their symptoms. For example, in diabetes, damages may arise in fundi, which damages should be discovered as soon as possible. Devices used for this are called oftalmoscopes or fundus cameras, and with those the inner parts of eye are examined by illuminating them through the pupil. Usually, when using a fundus camera, the person to be examined places her/his head into the examining device, and one or more trained person(s), such as a doctor, adjusts and moves manually the examining device and observes the object and, when necessary, launches manually the imaging device to take an image. Both eyes of the person to be examined are examined separately. This is a slow procedure and requires work contribution of a trained person.

Because the pupil of the eye contracts when light is directed thereto, the examinations are usually performed in a darkened room, and furthermore, eye drops can be used that enlarge the pupil and prevent it from contracting. Some patients, for example children, don't necessarily like applying of eye drops and recovering from the effect of them takes a long time. The patient and the nursing staff have to wait until the drops start to take effect before the examination can be performed. This slows down considerably the performing of the examination and also increases the threshold of the patient to go, for example, to routine examinations.

In patent publication WO 2010/051304, a device is disclosed which the user of the device, such as a doctor or an optician, can wear to the front of their own eyes to examine the eyes of the patient. The user of the device holds the device in front of the eye of the patient during the examination. The device emits infrared light and it is provided for turning the image prepared by the lens to correspond with the actual directions. The device described in the publication requires active participation of a trained person during the examination, and it is designed to operate only with infrared light.

In automated eye imaging one problem is that the devices become quite large and clumsy, when automatic focusing and similar properties are tried to be accommodated in the device. It would be a remarkable advantage if the size of the apparatus could be reduced such that even the person to be examined herself/himself could place the device in position and start the imaging. In practice, with the present technique even an automated device requires at least a trained assistant to use it.

SUMMARY

The object of the invention is a solution, by which the disadvantages and drawbacks of the prior art can be diminished. Particularly, the object of the invention is a solution, by means of which an automatically operating device for imaging an eye is provided that would work quickly and produce a reliable imaging result for diagnosis or monitoring without active operation of the device.

The objects according to the invention are achieved by a device, characterized in what is disclosed in the independent claim. Some preferred embodiments of the invention are disclosed in the dependent claims.

The main idea of the invention is to form a device for imaging an eye that can be worn on the object to be examined or otherwise placed to the front of an eye or eyes. The device has been reduced in size to be easier to operate by adapting the illumination and imaging to be directed in different directions in respect of the eye to be imaged. Thus, parts of the device required in imaging can be brought closer to the surface of the eye, whereby the device becomes smaller in respect of the prior art. This is accomplished by placing the illuminating and imaging arrangements apart from each other such, that their optical axes do not meet each other. When the device is switched on and placed in position or vice versa, the device automatically performs the imaging such that all images are useful. This is done by analysing the taken images or the image area, either in the device or on a server connected thereto, and when a reflection is detected in the image or image area the part in question is imaged again.

A device according to an embodiment of the invention is provided for examining an eye or eyes of a object, the device comprising one or more camera arrangements that comprises optics and a camera sensor, and the camera arrangement being provided for taking images or videos or both of the fundus or surface of an eye or both, and one or more illumination arrangements. In a preferred embodiment of the invention, the optical axes of the camera arrangement and illumination arrangement used in the same imaging are in different directions in respect of the eye, or they are substantially apart from each other. The device or a part of it, including at least the camera arrangements and illumination arrangements, are provided to be placed on the head of the object or to the front of the head of the object. The device is provided to be switched into an operation mode, which means that the device is in operation and active. The device comprises a control arrangement that switches the camera arrangement to take automatically one or more images of the eye, when the device is in operation mode and in front of the eye or eyes, and the control arrangement is provided to control the camera arrangement and the illumination arrangement. The device comprises an image analysing arrangement or a connection to an image analysing arrangement that is provided for detecting a reflection in the image taken by the camera arrangement or in the image area of the camera arrangement and for transmitting the information about the detected reflection to the control arrangement which is provided thereby to repeat or decline imaging.

In an embodiment of the device according to the invention, the device comprises a support construction which, in the operation mode of the device, is in contact with the skin around the eye, and the support construction surrounds the eye or eyes completely or partly.

In another embodiment of the device according to the invention, the device comprises a gaze guidance system for guiding the eye, and the control arrangement is provided to control the gaze guidance arrangement.

A third embodiment of the device according to the invention comprises an at least partly transparent part or a part that can be transformed into transparent, and the device is provided in a way that the movements of the eyes or an eye can be directed through this part with an external gaze guidance arrangement that is provided to be controlled by the control arrangement.

A fourth embodiment of the device according to the invention comprises a detector which is provided for detecting when the device in the operation mode is in front of the eye and when the eye is in a predetermined position in respect of the camera arrangement, and for transmitting a message to the control arrangement about starting the imaging.

In a fifth embodiment of the device according to the invention, the image analysing arrangement is provided for detecting deviations in images or image area and for transmitting the information about the detected deviation to the control arrangement which is thereby provided for repeating or focusing the imaging. By deviation a detectable and followable change is meant caused by a disease or similar.

In a sixth embodiment of the device according to the invention, when the control arrangement is repeating the imaging, it is arranged to control the camera arrangement, illumination arrangement or the gaze guidance system or a combination thereof or to mark the image in some way.

In a seventh embodiment of the device of the invention, the device comprises a motor arrangement for adjusting the direction or location of the camera arrangement or the parts thereof.

In an eighth embodiment of the device according to the invention, the motor arrangement is provided for directing the camera arrangement or parts thereof on the axes x, y or z in relation to the surface of the eye or pupil, when the device is in operation mode in front of the eye. In a ninth embodiment of the device according to the invention, the motor arrangement is further provided to move the camera arrangement or camera arrangements between imaging positions directed to different eyes.

A tenth embodiment of the device according to the invention comprises an individual imaging arrangement for both eyes that consists of one or more camera arrangements for both eyes, respectively, and for each imaging arrangement there is a motor arrangement, respectively.

In an eleventh embodiment of the device according to the invention, the control arrangement is provided to activate the motor arrangement, when the device is in operation mode and in front of the eye.

In a twelfth embodiment of the device according to the invention, the control arrangement is provided to guide the camera arrangement to take images, the object of which is based on an image mass taken previously from the person in question or collected from a large number of persons. In this way, imaging can be targeted at places that can be assumed to be interesting or are substantial from point of view of diagnosis. In a thirteenth embodiment of the device according to the invention, default values have been saved in the control arrangement for selecting the point of imaging.

In a fourteenth embodiment of the device according to the invention, the device comprises a data transmission system for transmitting the information obtained at least by the camera arrangement to an external service arrangement for storing or processing the information. In a fifteenth embodiment of the device according to the invention, the data transmitting system is provided for receiving from the service arrangement instructions for imaging that are characteristic to the object or that the service arrangement has calculated from the images of the object received previously and for transmitting the instructions for imaging to the control arrangement.

In a sixteenth embodiment of the device according to the invention, the device is provided for imaging a part of the fundus or surface of the eye at a time. The images can be formed into a mosaic.

In a seventeenth embodiment of the device according to the invention, the device is provided for measuring the shapes of the surface of the eye or the reflection properties thereof or both and for evaluating from these places of imaging or directions for imaging or both, the places of imaging or directions of imaging being in use by the control arrangement for switching the camera arrangement or guiding it to take images.

An advantage of the invention is that with it a device, automatically imaging an eye and fundus, is provided where the image quality remains good. Thus, repeating the imaging is avoided.

An advantage of the invention is that by means of it a device that is lighter and cheaper than the prior art can be provided that is easy to carry to different places.

An advantage of the invention is further that it is easy to be used by the object to be imaged.

Further, an advantage of the invention is that it is applicable to different types of eye imaging. The person to be imaged can also sit, stand or lay on a bed. Further, the invention reduces the time spent in a routine examination. Likewise, it reduces the need of trained personnel in such examinations.

An advantage of the invention is further that it enables automatic searching and quick checking of the detected deviations.

DESCRIPTION OF THE FIGURES

In the following, the invention will be described in detail. In the description, reference is made to the enclosed drawings, in which.

DETAILED DESCRIPTION OF FIGURES

The embodiments in the following description are disclosed as examples only, and someone skilled in the art may realize the basic idea of the invention also in some other way than what is described in the description. Though the description may refer to a certain embodiment or embodiments in several places, this does not mean that the reference would be directed towards only one described embodiment or that the described characteristic would be usable only in one described embodiment. The individual characteristics of two or more embodiments may be combined and new embodiments of the invention may thus be provided.

Figure 1:
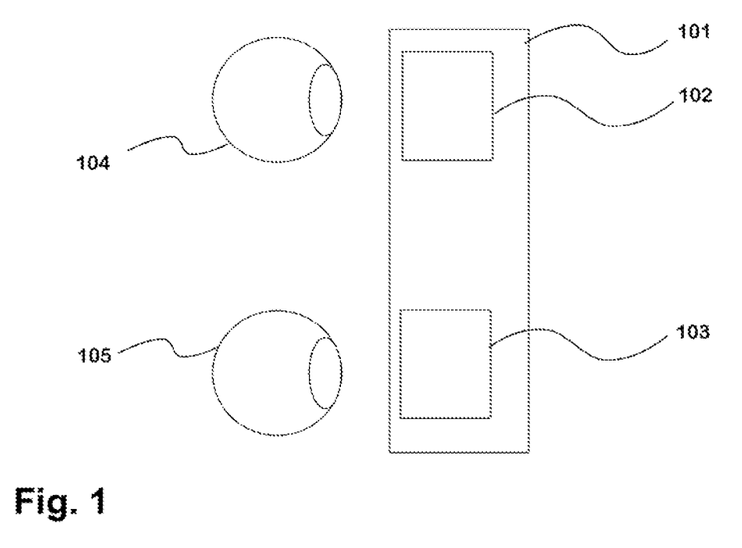
FIG. 1 shows an example of a device according to the invention.

FIG. 1 shows an example of the device 101 according to the invention. Let us remind in this connection that the images are simplified, in order to make the essential principle of the invention clearer. The device according to the invention can be realized by very many different formations.

Device 101 is meant to image eyes 104 and 105. The device comprises two camera arrangements: the first camera arrangement 102 and the second camera arrangement 103. The camera arrangements are placed in the device such that when the device is placed to the front of the eyes of the object both camera arrangements are substantially at their own eyes, respectively. There may be several camera arrangements per eye. The camera arrangements can be fixed, i.e. they have one imaging direction, or they are movable by the motor arrangement. With two camera arrangements the imaging can be performed for both eyes at the same time or nearly at the same time. The imaging can of course be performed in turn for each eye.

Figure 11:
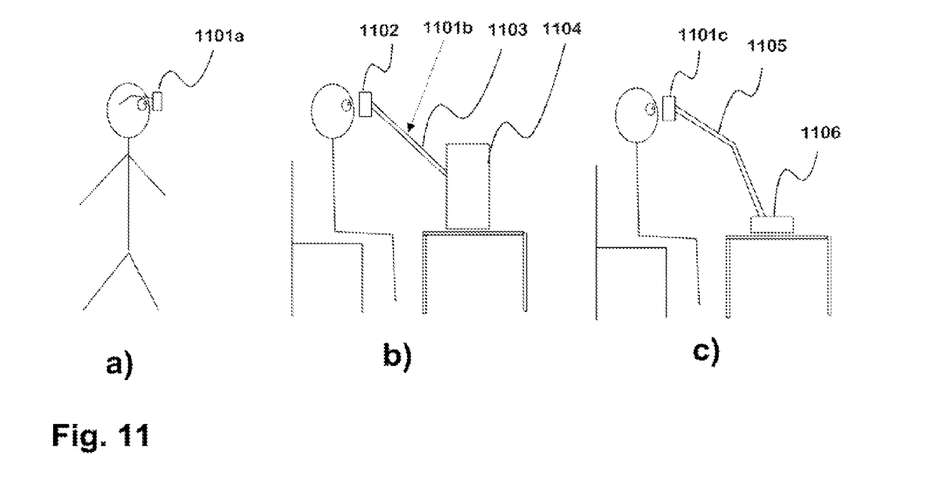

The device can be wearable on the object to be imaged, that is, it can be like the example of FIG. 11a, where it resembles eyeglasses, the frames of which are supported on the sides of the head. The frames can also extend behind the ears, or the frames can be short for the directing. A device to be worn on the object can be realized also in many other ways. It can, for example, resemble a cap or a helmet, and the imaging part of the device is in a visor that is lowered to the front of the eyes and positioned to the imaging position. The device can be realized such that it comprises a part which comprises at least camera arrangements and illumination arrangements, which part is placed to the front of the eyes correspondingly to the embodiment to be worn on the object. The part of the device to be placed to the front of the eyes is fixed to a movable structure which can be moved to different imaging positions depending on the object to be examined. Other functional parts of the device can be placed in a part that will not be worn on the object. Such an embodiment is shown in the example of FIG. 11b. Said other functional parts can, of course, be located in the part placed to the front of the eyes. Such an embodiment is shown in the example of FIG. 11c. This can be realized also without a support structure. The device can be realized also binocular-like, whereby the object of the imaging holds the device in front of her/his eyes. The part placed to the front of the eyes can be arranged to be movable such that the place or position can be altered, when it is at its position for the imaging event. This can also be arranged to be performed such that the person to be imaged adjusts the position of the device. This can also be done by the supervisor of the imaging, for example, if the object of the imaging is a child or otherwise not able to adjust the position. The position can be selected and adjusted also automatically. Thereby, for example, the motor arrangement of the device guides the support to be placed on the nose and thus places the device into the position where the imaging is performed. The device can also comprise other features by which the desired position is achieved and the device is made to stay there during the imaging. Such may include, for example, different stickers, suction pads, vacuum pumps or similar.

The device according to the example comprises a support structure which surrounds the eye or eyes completely or partly. By means of the support structure, the device can be supported when it is in its place, and by means of it the device can be positioned to the measuring position or close to it such that the device's own adjustment can be reduced. By means of the support structure the device can also be hold in its place during the measuring. The support structure is placed against skin. The support structure is made preferably completely or partly of resilient material in order to make its placing and wearing against skin more comfortable for the object.

The support structure can also be arranged to cover both eyes such that no diffused light gets to the eyes or the amount of it can be adjusted. Then, the device is at least partly against the skin of the object. The support structure is either completely or partly impermeable to light. Thereby, the eye is in a darker environment and the pupil of the eye can be made as large as possible prior to taking the image. For example, a transparent area can be left in the support structure for an external gaze guidance of the device. This transparent area can be realized, for example, so that on top thereof there is a cover that can be opened and closed such that it is useable only when necessary. The support structure, and similarly other parts of the device in front of the eyes, can be made such that, when necessary, it can be dimmed in a desired way at different places in order to reduce the diffused light in connection with the imaging. This can, for example, be realized such that the structure consists of two overlapping surfaces in different polarisations.

The device can naturally be realised also in a way that there is no actual support structure, but the device performs the imaging in front of the eye.

Device 101 comprises one or more illumination arrangements that can preferably be controlled. This may be in connection with the camera arrangement or separately. If the illumination arrangement is in connection with the camera arrangement, it can be arranged to be movable in the same time with the camera arrangement such that the illumination takes place in an advantageous direction from point of view of the imaging. The illumination arrangement can also be fixed, i.e. it is directed into a certain direction. The device may also comprise more illumination arrangements that are directed in different directions, and those can be used alternately. The illumination arrangements can operate, for example, in visible light and infrared light areas. The different illumination arrangements of the device can operate in different wavelength regions. The illumination arrangements can be realized, for example, by LED lighting fixtures, halogen technique, laser, bulbs or in some other way. The illumination arrangements can operate by being switched on for a predetermined time or by producing a flashlight type flash. If the illumination arrangement is able to be directed, it is moved by the motor arrangement. The illumination arrangement can include optics which can be adjustable, for example, for positioning of the light. The illumination arrangements are situated in respect of the camera arrangements in a way that they are separated from each other so that their optical axes do not meet.

Substantially, in the imaging of the eye, the camera arrangement and the illumination arrangement are situated in respect of the eye in a way that the optical axes of the camera arrangement and the illumination arrangement in respect of the eye are of different directions or substantially apart from each other. Thereby, the imaging of the eye and the illumination are performed from different directions or at least from different locations. These directions or locations are preferably adjustable, i.e. the location or direction or both of the camera arrangement or the illumination arrangement or both can be changed. Thereby the directions of the imaging and illumination change. Changing the directions of the imaging and illumination may lead to a situation where their optical axes in respect of the eye would be in the same direction. Thereby, said optical axes are however, substantially apart from each other. In addition to the change of directions of the imaging and illumination, also changing of the position of the eye in respect of the imaging and illumination can be used. Then, a gaze guidance arrangement is used which will be described later. When the illumination and imaging are in different directions, i.e. the directions of the camera arrangement and the illumination arrangement in respect of the eye are different, no beam splitters are required in the device, and also the amount of other components can be reduced. Since also the illumination arrangement and imaging arrangement can be situated closer to the surface of the eye than in prior art, the device can be formed smaller than the devices of the prior art. Since the directions of the illumination arrangement and the camera arrangement in respect of the eye, and, when necessary, also the position of the eye can be changed, the imaging event can be optimised by means of the control arrangement and image analysing arrangement (will be described later). In this optimisation the positions of the illumination arrangement and the camera arrangement in respect of the surface of the eye are changed and the combination of positions is selected that is best suitable for the imaging event.

When the illumination and the imaging are in different directions, the illumination arrangement and the camera arrangement do not go in the way of each other, that is, they are at such distances from the surface of the eye and situated to each other in a way that they do not cover each other. Because the positions of the illumination arrangement and the camera arrangement in respect of the surface of the eye can be changed, an embodiment can be realized where the direction of light is random, and during the imaging the direction of light is selected that is the best for the imaging in question. Thus, the light is directed to the fundus of eye from a random spot in relation of the camera arrangement, in order to be able to perform the imaging as quickly as possible and without any special arrangements used in prior art for aligning the head, eye, pupil and fundus in respect of the imaging light of the fundus of eye on the same axis and in respect of the light coming onto the camera arrangement. In the invention, minimizing of the imaging arrangements results, however, in harmful reflections coming from the surface of the eye.

When the imaging and the illumination are divergent, a situation will become obvious whereby the light of the illumination arrangement is reflected from the surface of the eye to the camera arrangement. Since this reflecting light is substantially brighter than the data aspired after in the imaging, the reflecting light, i.e. reflection impedes the imaging and, in the worst case, ruins the whole imaging. This is difficult to evaluate in advance with different persons to be imaged, since the amount and character of the reflections depend partly on the humidity of the eye and the shape and position of the eyeball. In the invention, this problem is excluded in a way described later.

The device according to the example comprises a power supply for operating the different parts of the device. This may be an accumulator or a battery or a connection to an external power supply, or similar. The device can also be provided to be charged by placing it in a dock charger or to charge it by wireless means. This is not shown in the figures. The device further comprises an arrangement by which is switched on. This may be, for example, a switch, the switching of which causes initialization of the functions of the device and moving to the operation mode. The device may also comprise some other arrangement, by which it is moved to the operation mode. In the operation mode, the device can check whether it is in its position in the front of the eyes. This may have been realized, for example, by different detectors. The part of the device to be placed in the front of the eyes may comprise an electronic or mechanical detector to detect whether it is pressed against the skin. This can also be realized by identifying reflection properties of an eye or eyes. In detecting the distance, also an image analysing programme can be used, where, for example, the size of the eye is recognized or the camera arrangement is focused as a default for a predetermined distance, and when the image is sharp, the imaging area of the camera arrangement or the operating area of its own focusing motor is reached. The device can also be started manually to perform the imaging when it is placed in its position. This can be done by the supervisor or object of the imaging when he/she feels that the device is placed in its position. The device is provided also for switching itself off or for shifting to a standby mode when the imaging was performed acceptably. The device can further be realized such that it is placed in a dock charger or similar arrangement and it starts when it is removed from the dock charger and switches off when it is returned to the dock charger.

The device may comprise a motor arrangement that consists of one motor or more. It is provided for moving the movable parts of the device that can include the camera arrangement, different optics, illumination arrangements and different covers. For example, the part of the device, through which the eyes are being imaged, can be covered when the device is switched off or in standby mode, in order to prevent dirt or excessive light from going into the device, which can impair the camera sensors of the camera arrangements.

The device comprises a control arrangement for controlling the parts and functioning of the device. This may have been realized by means of a memory or one or more processors, and the operating procedures are stored in the memory and are performed in a processor in order to give operating commands to different parts of the device. The control arrangement may also be an embedded system. The control arrangement is provided for transmitting and receiving data. The control arrangement can, for example, transmit the images taken by it forward, and it can receive imaging instructions or other data related to its operation. The device also comprises an image analysing arrangement or a connection thereto, which arrangement analyses the images taken by the device, or directly data coming from a camera sensor. The image analysing arrangement is provided such that it operates in real time or almost in real time, i.e. it performs an analysis for an image taken by the camera arrangement of the device as soon as the image was taken, and preferably before the next image will be taken. The image analysing arrangement comprises an arrangement to contact the control arrangement.

The control arrangement controls the operation of the camera arrangements and illumination arrangements, i.e. the fact when and where images are being taken from and how the illumination operates. The control arrangement can have an instruction for imaging stored in its memory which instruction can, for example, guide to image a part of retina that one is interested in. The control arrangement guides the camera arrangement to take one image or a series of images from the desired point, which images are combined in an entirety in the device or, for example, in an external server. The parameters of the images, i.e., for example, from which point the image will be taken, at which distance, with what kind of illumination, with which camera arrangement, with which duration of illumination and similar, can be changed for example by changing the operation and positions of the camera arrangements and illumination arrangements or by changing the position of the eye by means of a gaze guidance arrangement, or by combinations thereof. The gaze guidance arrangement is described later in connection with FIG. 6.

The control arrangement can receive external commands, for example, in order to perform the imaging at the same time as it performs its stored commands. For example, part of the operation of the cameras can be controlled from outside of the device, and part of the operation of the cameras from the device.

The control arrangement guides the image to be checked by the image analysing arrangement. For example, the image analysing arrangement checks whether there are reflections in the image taken or in the image area, i.e. whether there is light of the illumination arrangement reflected from the surface of the eye. Thereby, no data can be obtained from the image, and the image is useless either completely or partly. The image analysing arrangement can perform this checking, for example, by means of the pattern recognition automatism when the reflections are clearly recognizable shapes in the image, or for example by studying the values of the pixels of the image or the values of the real-time image information obtained from the camera and by detecting the reflection included in the image, if the values of a pixel group exceed a given limit value. These can be done also directly from the camera sensor without actual imaging. The reflections are nearly always brighter than the aspired image data. When the image analysing arrangement detects a reflection, it transmit the data to the control arrangement. Thereby, the control arrangement performs re-imaging of the spot in question and changes the parameters of the imaging, such as, for example, the positions of the illumination arrangement or imaging arrangement or the eye positions by means of the gaze guidance arrangement, or combination thereof such that there will be no reflection in the new image. The image or area including a reflection can also be ignored, if, for example the imaging area is compiled from a large number of separate images, and an individual image is small in comparison with the total image, or the reflection area is small in comparison with the complete image. Imaging or a part of the imaging is repeated, if there is a significant number of omitted images due to reflections or if they are situated such that there are significant apertures in the total image, i.e. points about which no information exists to be used. In addition to reflections, deviations can be looked for in the images, discovering of which may, for example, transfer the control arrangement to guide the imaging arrangement to take new images with new parameters. A new imaging can be performed, for example, in a greater resolution in the vicinity of the detected point or with a different imaging mode like by using a different wavelength camera or a different illumination or a camera of a more accurate imaging area. Absence of data can also be considered as a deviation. The image analysing arrangement can also study whether there are reflections in the image area of the camera arrangement, i.e. the situation is checked before the actual imaging. The image analysing arrangement can also use camera arrangements or camera sensors which are provided for observing reflections before the actual imaging. This camera arrangement or camera sensor may exist only for this purpose.

The image analysing arrangement can also be provided for checking whether the shape of the eye is suitable for imaging. Or it can check if there is some other disadvantage in the image because of which the image can not be considered to be accepted as a storable image. The image analysing arrangement and the control arrangement can also make a note, if imaging is repeatedly unsuccessful in some area or imaging direction or illumination or gaze guidance parameters or with a combination thereof. This may mean that on the surface of the eye or elsewhere in the eye there is damage or some other feature that prevents the imaging. The image can also be arranged to be storable even if one of its areas is useless. A note can also be made in the image if an above-mentioned deviation was detected therein. The note in the image may be, for example, a graphic addition in the image or title of the image or an addition is made in its metadata. Further, a file can be made which is either attached to the image itself or exists separately, which file includes a note about the image including a deviation. The control arrangement can naturally indicate the supervisor of the imaging by a sound or light signal or similar.

The control arrangement can also in connection with the imaging with the image analysing arrangement detect the change in the size of the pupil of the eye and control the imaging considering the change of the size of the pupil. The control arrangement can, for example, guide the camera arrangement to take as many successive images as possible before the pupil is too small. For this, for example, illumination time, speed of the camera shutter, direction of the shutter, amount and direction of light or other parameters can be used.

After the imaging the control arrangement performs the final procedures, which may include transferring the taken images to an external server for storage or further processing, and thereafter switches the device from operation mode to standby mode, where the device is ready for moving from a signal again to operation mode, or switches off the device. The final procedures may further include an automatic recommendation for additional imaging or a new checking after a certain time. The recommendation may be based on the image analyses or medical data of the patient.

Thus, the imaging can be performed automatically and quickly without the need of participation in imaging by trained personnel.

Further, other sensors may be connected to the device 101 according to the invention. These may include, for example, temperature measuring, different chemical analyses, different measurements, such as, for example, tonometry, and similar. The device can also comprise action sensors which can include, for example, laser and different dosage arrangements of medicines or similar. The device can also comprise an accelerometer or sensors for measuring the position of head. Accelerometers can be used also for measuring movements, of the head and possibly for compensating them for the imaging. Also other position or location identification means can be applied to the device. The device can further comprise an image stabilization system, and accelerators and other position or location identification means can be used in assistance thereto. The device can further comprise, for example, a magnetometer, gyroscope arrangements or pressure transducers.

A display or displays can be provided in the device on the side of the eyes or in the front side of it or both. For example, the front side display can be provided for indicating the progress of imaging. Further, real-time image taken by the camera can be transmitted to it. Further, a microphone and a loudspeaker can be connected to the device. The device can also use a microphone and loudspeaker existing in its near vicinity. The object to be imaged can, for example, give a voice message as soon as he/she is ready for starting the imaging, or tell the device instructions related to its operation. By means of a loudspeaker, one can give, for example, a sound signal when the device is in its position for imaging or when the person to be imaged is instructed to look in a certain direction. Further, an embodiment may exist, where a picture is shown to the person to be imaged, and he/she has to tell what is in the picture. Speech or comments of the person to be imaged can also be recorded, and these can be used later, for example, to assist diagnosing.

The device or a part of it can also be realized as a part of some other device, such as for example a smart phone or a similar device. Thereby, for example, the camera of a smart phone and optics connected to the front of it could form a camera arrangement of a device according to the invention.

Figure 2:
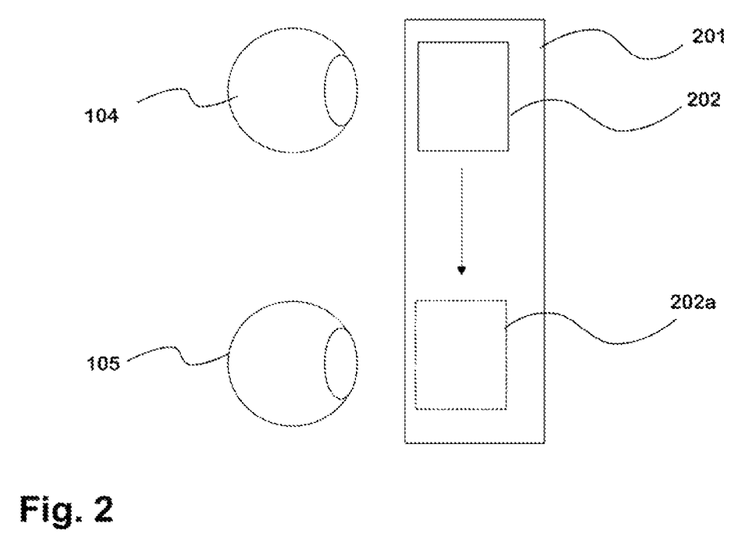
FIG. 2 shows another example of a device according to the invention, FIG. 3 shoves an example of a camera arrangement according to the invention.

In FIG. 2, a second example is shown of a device 201 according to the invention that is meant to image eyes 104 and 105. The device according to the example is otherwise similar to the one shown in FIG. 1, but it comprises one camera arrangement: camera arrangement 202. In the example, the camera arrangement is first in front of the eye 104. As soon as the eye in question is imaged, the motor arrangement moves the camera arrangement to position 202a to the front of the other eye 105, whereby it can be imaged. Also an arrangement is possible, where the device is turned upside down, and the camera arrangement is then positioned in front of the other eye. Further, an arrangement can be provided, where the camera arrangement is in front of the one eye and in front of the other eye there is a gaze guidance arrangement, and their positions are exchanged when the eye to be imaged is changed.

Figure 3:
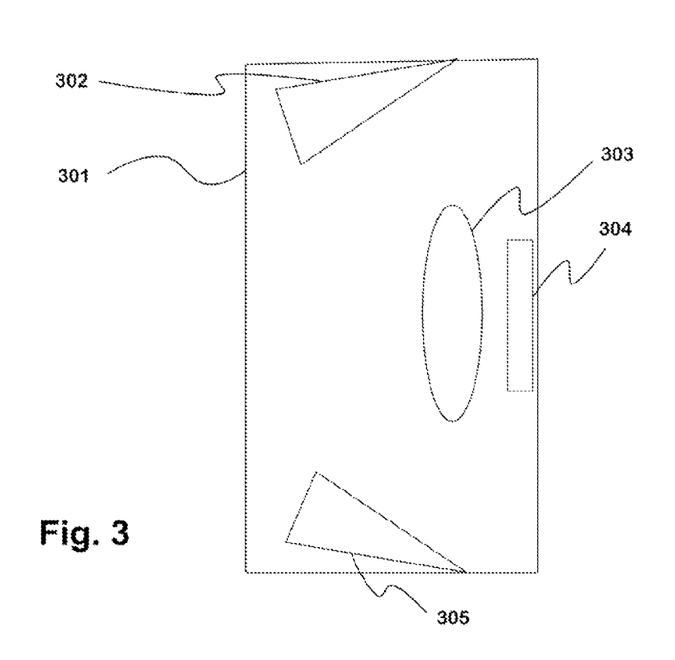

FIG. 3 shows an example of a camera arrangement 301 according to the invention. The camera arrangement according to the example comprises optics 303 and a camera sensor 304. Furthermore, in this example the camera arrangement comprises a first illumination arrangement 302 and a second illumination arrangement 305. The illumination arrangements do not need to be in connection with the camera arrangement, but they can also be located separately and individually. Usually, by an illumination arrangement the object to be imagined is illuminated, but they can also be used, for example, in measuring of distance or to reflect dynamic patterns to lens of the eye, vitreous body or fundus. The illumination arrangements can be movable, i.e. their location or direction or both can be changeable or adjustable. This is accomplished by a motor arrangement connected with the illumination arrangement, which motor arrangement is controlled by the control arrangement.

The camera of the camera arrangement 301 consists of optics 303 and camera sensor 304. The camera sensor can be formed of one or more photosensitive parts. These photosensitive parts can detect for example visible light, IR or UV radiation or a restricted wavelength area. The camera sensors can be realized, for example, by a multispectral or hyperspectral technique. By a camera arrangement images or videos can be produced. A camera arrangement can be provided for monitoring by means of IR radiation reflection points of an eye and for storing them for use during the actual imaging.

The optics 303 can be fixed or arranged to be movable or detachable. The optics can be adjustable, i.e. it can be for example, focused. This can be performed by a motor arrangement. These focusing and other adjustments can be realized also by moving the camera sensor or by moving the both: the camera cell and the optics. The optics may consist, for example, of one or more lenses with different refractions or of a prism, the bevels of which comprise one or more sensors and illumination arrangements. Both the lens technique and the optics realized with a prism and the camera sensor related thereto can possibly be dimensioned such that it covers the whole area of the eye or that several pairs of optics and camera sensors can be accommodated in the area of the pupil for imaging of the fundus. One part of the camera sensor can use several optics of different size or a combination thereof. Likewise, one set of optics can be arranged to direct the light to several different sensors simultaneously. Further, in combination with the optics there may be dimmers or shutters or other similar parts. The optics can also be realized, for example, by liquid optics. It is essential that the optics is provided for directing the light in a desired way to the image sensor for performing the imaging.

In addition to moving individual parts, the camera arrangement can be movable also as a whole like in FIG. 2. This can be realized by a motor arrangement. A possible motor arrangement is realized such that the motor arrangement guides the camera arrangement by possible axes x, y and z in relation to the surface and pupil of the eye. The motor arrangement can also be adapted to rotate or incline the camera arrangement. The device according to the invention can comprise several solutions like in FIG. 3 or several divergent solutions, and they can be changed according to the imaging mode or object of the imaging. For example, a camera arrangement can be meant for exact imaging of the fundus and another one for general imaging.

The control arrangement is provided for controlling the pair of optics and camera sensor of the camera arrangement 301 and the first illumination arrangement 302 and the second illumination arrangement 305 automatically, according to its instructions. An illumination arrangement best suitable for each imaging case is selected. The control arrangement can perform the detecting of the object and focusing on it by the camera arrangement. Further, it can remove the effects caused by shaking and other movements from the camera sensors or optics or both. This is accomplished by means of accelerators, gyroscope arrangements or similar detectors of movement and location such that when a movement is detected, a contrary movement is made to the camera arrangement or to a part of it.

Figure 4:
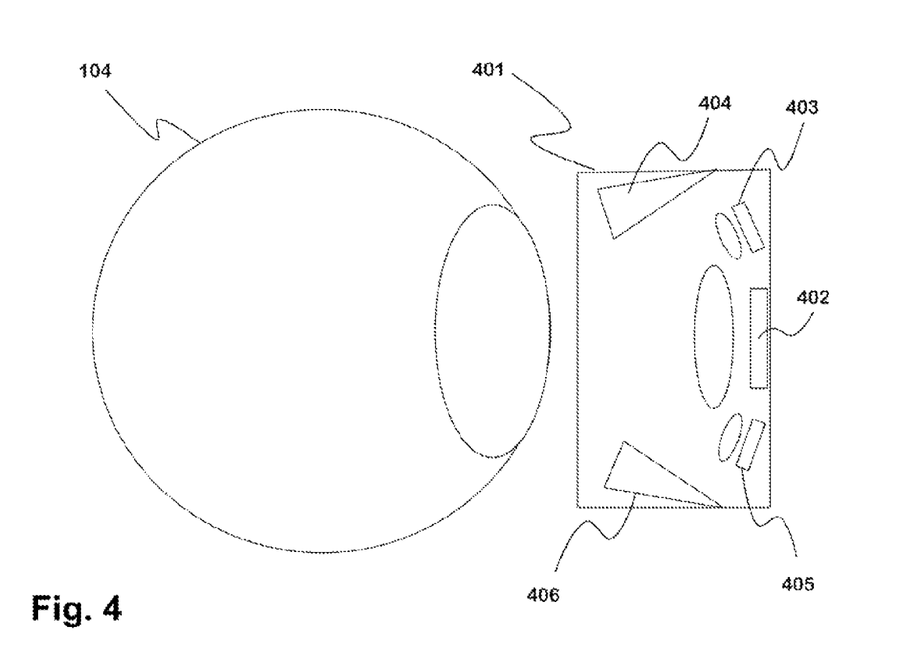
FIG. 4 shows another example of a camera arrangement according to the invention in an imaging situation.

FIG. 4 shows another example of the camera arrangement 401 according to the invention that is in the front of the eye 104 in the imaging situation. The camera arrangement comprises a first illumination arrangement 404 and a second illumination arrangement 406. In this example, the camera arrangement comprises three pairs of optics and camera sensors: the first pair of optics and camera sensor 402, the second pair of optics and camera sensor 403 and the third pair of optics and camera sensor 405. Naturally, there can be some other amount of pairs of optics and camera sensors. The pairs of optics and camera sensor may be movable in relation to each other or they are fixed in their places. The pairs of optics and camera sensors can also be located such that with them the imaging area can be covered such that the camera arrangement or parts thereof do not need to be moved. This is how it is done if the image analysing arrangement does not detect predetermined features in the images, such as reflections or deviations. If, for example, a reflection is detected, the control arrangement, for example, changes the illumination arrangement, and the imaging is performed again, either at required place or totally again.

If small camera sensors in relation to the object of the imaging, i.e. the eye, and thus also optics with long focal length and small viewing angle are used in the device according to the invention, several of these pairs of optics and camera sensors can be placed close to the surface of the eye. Thus, for example, a small part of the fundus can be imaged at a time. The final result is an image mosaic of the fundus. The images of the mosaic can be partly one on top of another, and some partial images can be one on top of another. In this way, for example, images taken of the same area with different wavelengths or different imaging modes can be combined. A short focal length and optics close to the surface of the eye reduce the amount of reflection from the surface of the eye, if the angle of the incident light is such that the light source is not visible in the image because of the distance of the imaging optics close to the surface of the eye, so by this, the need of repetition of imaging can be reduced. The pairs of optics and camera sensors can be placed at different distances in relation to the surface of the eye. Thereby, the pair of optics and camera sensor is used that is best focused in relation to the object of the imaging. Thus, moving of the pair of optics and camera sensor can be avoided or reduced.

Figure 5:
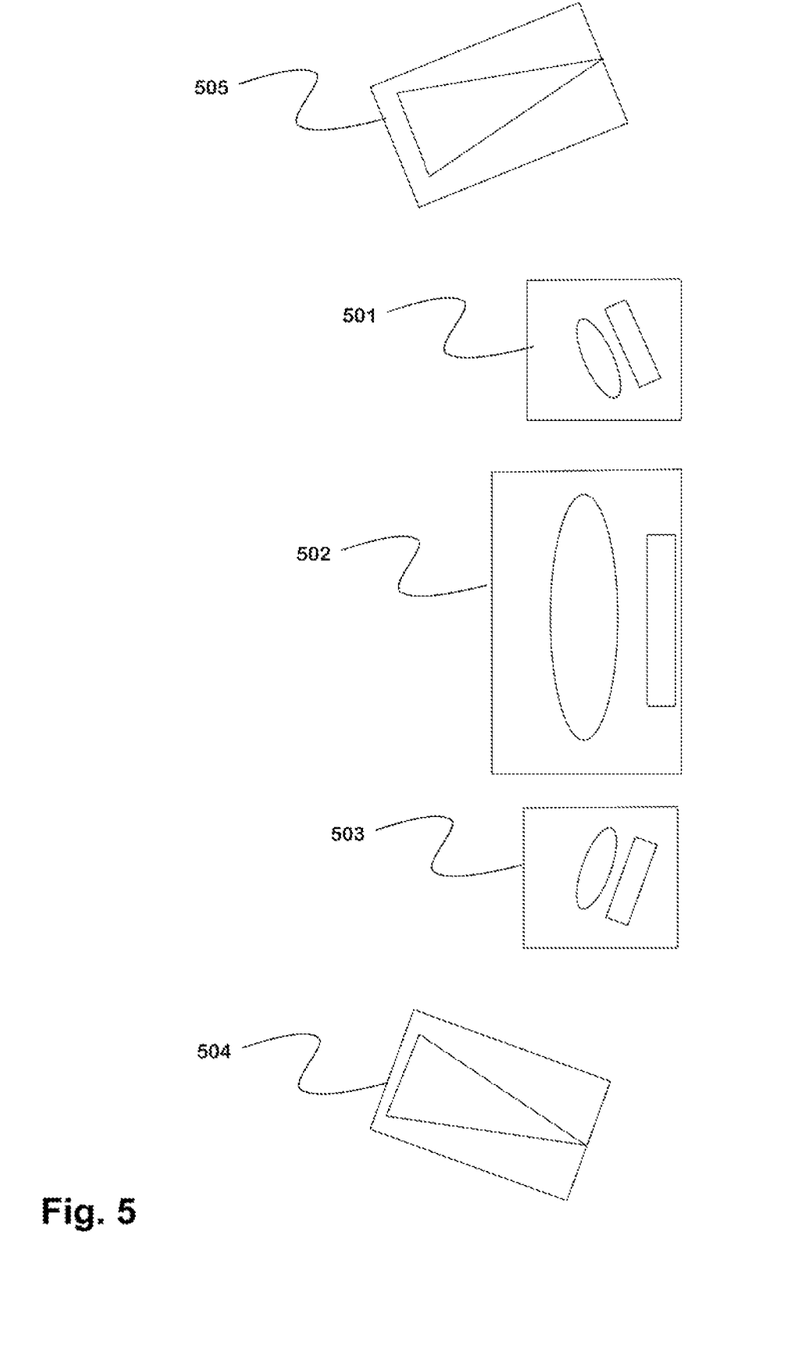
FIG. 5 shows an example of an imaging arrangement according to the invention.

FIG. 5 shows an example of the imaging arrangement according to the invention that consists of three camera arrangements: the first camera arrangement 501, the second camera arrangement 502 and the third camera arrangement 503, and two illumination arrangements: the first illumination arrangement 504 and the second illumination arrangement 505. In the example, the camera arrangements and the illumination arrangements form separate modules that can be movable separately or fixed independently of each other. The camera arrangements and the illumination arrangements can be different as to their features. Illumination arrangements can be moved, for example, around a camera arrangement or they can be directed according to the object of imaging of the camera arrangement. Instead of movements of the single parts of the imaging arrangement or in addition thereto, the imaging arrangement is movable as one entirety.

In a case according to the example where there are several camera arrangements at different angles and distances, figuring out of surfaces and other three-dimensional shapes and adding this information to the images or other files can be enabled. A three-dimensional imaging can, of course, be realized by means of one camera arrangement by imaging the same point from different angles.

Figure 6:
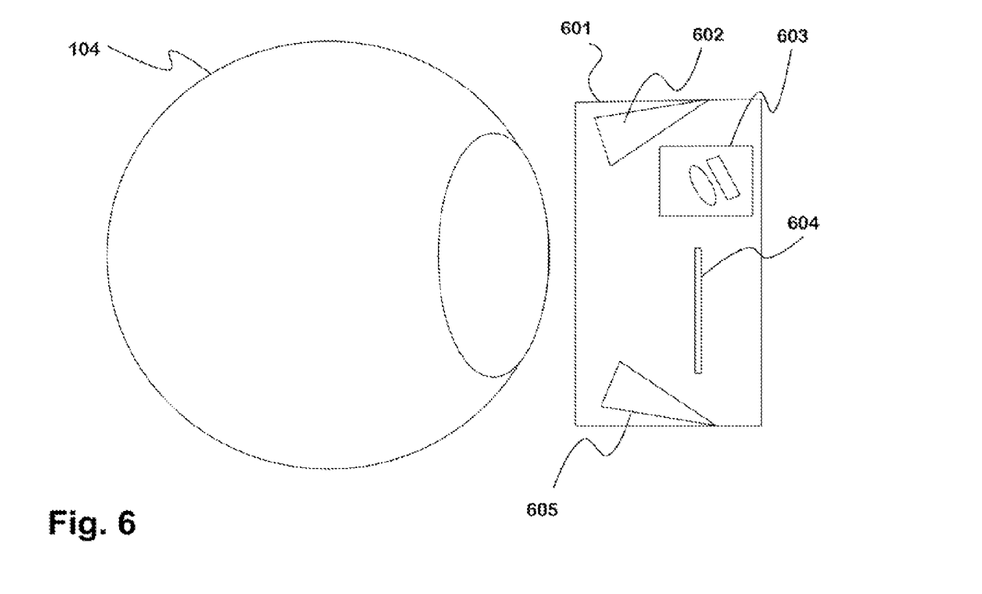
FIG. 6 shows another example of an imaging arrangement according to the invention in an imaging situation.

FIG. 6 shows another example of the camera arrangement 601 according to the invention that is in the front of the eye 104 in the imaging situation. The camera arrangement comprises two illumination arrangements: the first illumination arrangement 602 and the second illumination arrangement 605, and a pair of optics and camera sensor 603. Further, the camera arrangement comprises a gaze guidance arrangement 604. The gaze guidance arrangement guides the object to be imaged to look at certain directions such that the camera arrangement gets the next imaging area to be imaged. The gaze guidance arrangement is further provided for guiding the eye to a position where no reflection takes place or it is minimized when the image analysing arrangement detects a reflection in the image taken or in the image area before imaging. Correspondingly, the gaze guidance arrangement can be provided for guiding the gaze such that the same patient can be imaged every time at the same place or in the same position of the eye. Thereby, the guiding parameters of the gaze guidance arrangement are stored in a patient-based file that is introduced when starting the imaging. The control arrangement can download this file, for example, from an external server. The gaze guidance arrangement can be a display, for example a LCD display, where a dot, figure or area or similar is shown that the patient is supposed to look at. This object of the gaze is moved according to how and to, which position the eye is desired to move. The gaze guidance system can also be realized, for example, by a laser light, or the gaze guidance pattern is reflected directly onto the retina of the eye. The gaze guidance system can also be moved by a motor arrangement. Operation of the gaze guidance arrangement is controlled by the control system based on the imaging to be performed.

By the gaze guidance arrangement an embodiment can be realized, whereby the device does not comprise a motor arrangement designed for moving the camera arrangement, but the controlling of the imaging is realized merely by gaze guidance, i.e. the eye is guided to different positions in the imaging field and thus the imaging area is covered. Movements of the parts of the device and the gaze guidance can also be combined. Imaging can also be realized such that by the gaze guidance arrangement the gaze of the object to be imaged is guided to certain spots, and the camera arrangement takes an image or images, and the direction of the imaging of the camera arrangement is slightly adjusted. Thus, the movements required by the camera arrangement can be reduced in comparison with a situation where the gaze direction of the object remains unmoved, and the equipment can be simplified.

In this example, the gaze guidance arrangement is provided in connection with the camera arrangement. The gaze guidance arrangement can naturally be also elsewhere in the device.

Figure 7:
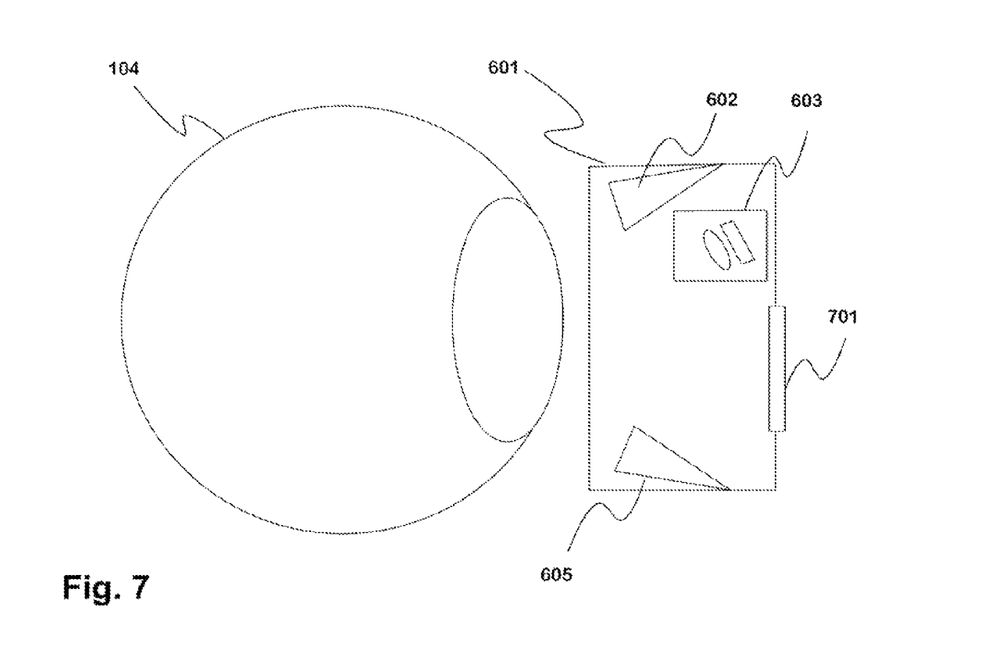
FIG. 7 shows a third example of an imaging arrangement according to the invention in an imaging situation.

FIG. 7 shows a third example of the camera arrangement 601 according to the invention that is in the front of the eye 104 in the imaging situation. The camera arrangement is otherwise similar to the one in the example of FIG. 6, but here the place of the gaze guidance arrangement is at least partly taken by a light transmitting surface 701. The gaze guidance system can be, for example, a pattern shown on a display or reflected to the opposite wall that is visible through the surface in question. By movements of this pattern the gaze direction of the eye 104 is guided correspondingly to what was described in connection with FIG. 6. This light transmitting surface can be protected by a plate or similar that is moved away from the surface when the gaze guidance is required. It is not necessary to guide the gaze through a camera arrangement, but a described light transmitting surface can be also elsewhere in the device substantially in front of the eye to be imaged.

Figure 8:
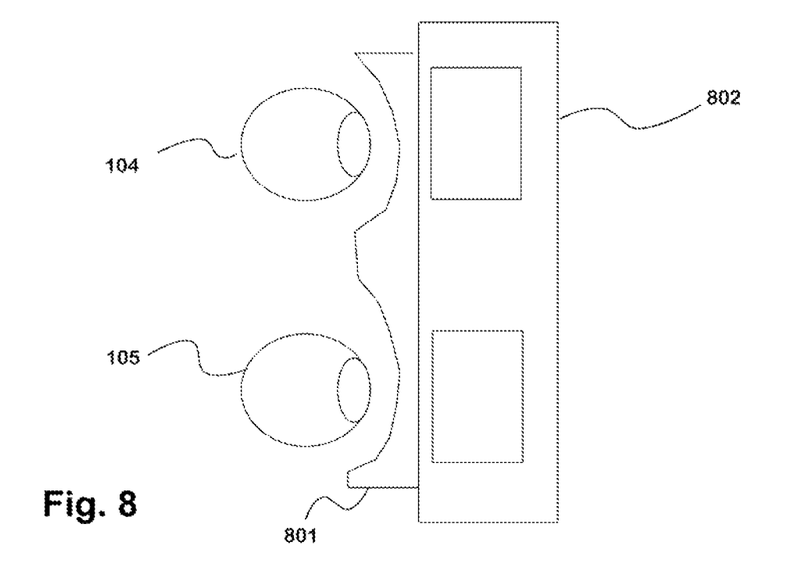
FIG. 8 shows a third example of a device according to the invention.

FIG. 8 shows a third example of a device 802 according to the invention. The device comprises a support structure 801 that covers the both eyes 104 and 105. The support structure is preferably made of an elastic material, or at least the parts to be placed against the skin are elastic in order to make the support structure to be placed tightly against the skin so that no light can escape from between the skin and the support structure to the eyes. The device can comprise an arrangement, by which it is pressed in its place. These may include adjustable handles or bands or similar, by means of which the device is put in its place. The device can also be connected to a helmet-like structure that includes a part to be placed to the front of the eyes. The device can also be such that the user does not wear it but the device is held on a support and the user pulls it to the front of her/his eyes and places it in its position by herself/himself. The device can also be supported on a support so firmly that the user can lean on the device, and thereby the support structure settles around the eyes. The device can also be binocular-like, and the user holds it in place by herself/himself.

Figure 9:
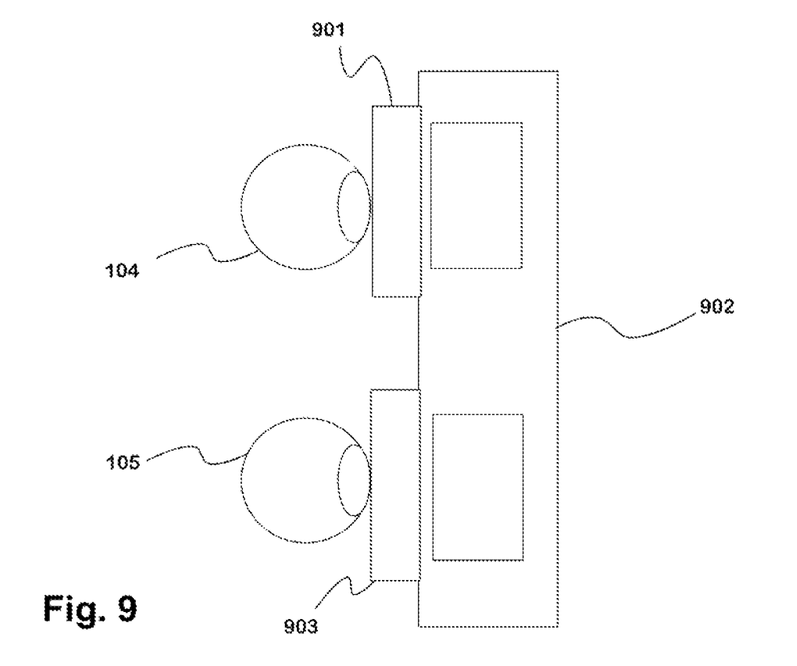
FIG. 9 shows a fourth example of a device according to the invention.

FIG. 9 shows a fourth example of a device 902 according to the invention. The device comprises two support structures: the first support structure 901 and the second support structure 903. Both support structures are for one eye, respectively. The distance of the support structures is adjustable according to the distance of the eyes of the user. The support structures can be changeable. Preferably, on the surface of the support structure laying against the skin a cover can be placed that is changeable after each patient, or the surface of the support structures is easy to clean, for example, with a disinfectant or a detergent. This improves the hygiene of the devices.

Figure 10:
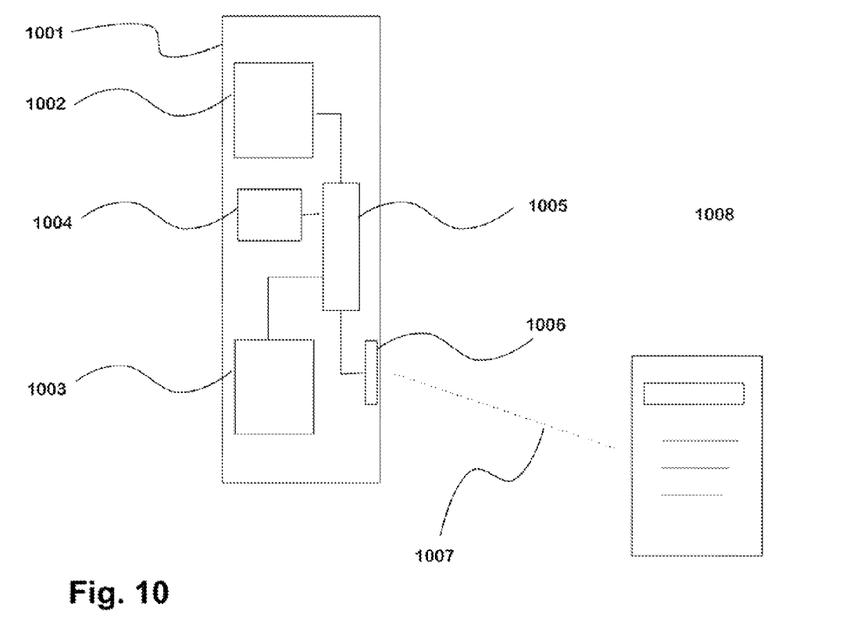
FIG. 10 shows a fifth example of the device according to the invention and an external service arrangement and FIG. 11 shows different applications of the device according to the invention.

FIG. 10 shows a fifth example of the device 1001 according to the invention and an external service system 1008. The diagram of the example shows the first camera arrangement 1002, the second camera arrangement 1003, the control arrangement 1005, the image analysing arrangement 1004 and the communication unit 1006 to make a connection 1007 with an external service arrangement.

The control arrangement 1005 guides the camera arrangements to perform the imaging. At the start of the imaging the control arrangement can receive instructions from the external service arrangement. These instructions may be patient-based and therein the device can be guided to examine a certain point in the eye that is desired to be monitored. The device comprises an image analysing arrangement 1004 with which the control arrangement is in connection. The control arrangement transmits the image taken by the camera arrangement, or in case of a video image, a shot of video image flow, to the image analysing arrangement that analyses the image and returns to the control arrangement an indication of the state of the image. This indication can, for example, show that the image is proper and imaging can be proceeded, or that there is a reflection in the image and the point has to be imaged again, or if the image taken is small in relation to the total area to be imaged. It can be discarded, or that a deviation was detected in the image and the area should be imaged more accurately. This deviation can be detected, for example, by comparing the image with a reference file that was provided, for example, from the previous images of the patient or from data collected from a large number of persons. Reflections or other artefacts related to the imaging, such as for example inaccuracy, are detected by an image analysing method, such as pattern recognition or based on the expected values of deviations of the values of the image pixels. Deviations in the images can also be looked for by means of pattern recognition. The image analysing arrangement can also be outside of the device or the part of it which is placed to the front of the eyes. Thus, the control arrangement aims at controlling the imaging in real time or as closely as possible to real time. Progress of imaging depends on the quality or results of the previous imaging procedures. The control arrangement reacts to the messages received from the image analysing arrangement, for example, by changing to a camera arrangement producing more accurate images or to another wavelength area, or, for example, when avoiding reflections or other artefacts, by changing the features of the imaging, such as position of the camera, direction of the illumination, position of the eye, or different combinations thereof. The control arrangement can also direct the eye by means of the eye guidance system to a preferred position. The control arrangement can also be arranged to identify the object by comparing an image taken of the eye of the object with an image in the database which identifies the object. This image may, for example, be of the iris of the eye or the fundus of the eye. The database can be located in the device or an external server.

The device according to the FIG. 10 comprises a communication unit 1006 that forms a connection 1007 between the device and the external server 1008. The communication unit operates either wireless, i.e. a radio connection or similar is used, or fixedly. The communication connection can also be arranged to be used by both communication types, i.e., for example, it receives the instructions for imaging and other necessary information wireless, and after the imaging the image files are transferred through a fixed connection. In this connection, the device can also be recharged. This may help the imaging, when during imaging there is no need to have a data transmission cable connected with the device. The device may have been realized further in a way that it comprises separate part to be placed to the front of the eyes and a second part that can be held, for example, on a table. The part in front of the eyes at least comprises the parts required for imaging and the communication unit that transmits information between the part in front of the eyes and the other part. The control unit, or at least part of it, may exist in the other part. Thus, the part required for the imaging can further be lightened, when necessary, and the imaging event made even easier for the person to be imaged.

The external server 1008 preferably includes the databases and other information needed for performing the imaging. The images taken by the device can also be stored therein. The image analysing system can be provided in the external server. Thus, processing efficiency required for performing the imaging can be shared. The images can naturally be stored in the device's 1001 own memory from where they are viewed by reading the memory of the device.

FIG. 11 shows different examples of ways in which the invention can be carried out. FIG. 11a shows an example of a wearable embodiment of device 1101a according to the invention that resembles eyeglasses. In FIG. 11b, the device 1101b comprises the first part 1102 and the second part 1104, connected by a support arm 1103 that is meant to be movable. The first part is provided to be placed to the front of the eyes. The user either presses her/his face against the first part or presses it against her/his face or places it to the front of her/his face at a suitable distance. When necessary, for example, a strap can be placed over the head that guides the head to the right position in relation to the first part. The functions of the device are divided between the first and the second part. Thereby, the first part comprises at least the parts related to the imaging, which include the camera arrangements, the illumination arrangements, the eye guidance arrangement and the motor arrangement designed for moving them. It is to be noticed, that ail said parts are not necessary in all embodiments, FIG. 11c shows the device 1101c, attached to the support part 1106 by support arm 1105. The support part is so heavy that it holds the device firmly in its place, or it can, for example, be fastened to a table. Otherwise the device corresponds to the device of the example of FIG. 11a.

The device can be realized also in many other ways. The device can, for example, be a tubular structure movable by the user, for example, in a mask covering the eyes along bars over the eye to be imaged. Thereby the mask can include a cover that covers the eye that is not being imaged. Also an embodiment can be realized where the other eye needs not to be covered. This can be, for example, a tubular structure that is placed over one eye or to the front of one eye at a time.

Above, some preferred embodiments according to the invention have been described. The invention is not limited to the solutions described above, but the inventive idea can be applied in numerous ways within the scope of the claims.

The invention claimed is:

1. A device, for examining at least one eye of an object, the device comprising:
   one or more camera arrangements, each camera arrangement comprising optics and a camera sensor, each camera arrangement being configured to take imaging of at least one of the fundus of the at least one eye and the surface of the at least one eye;
   at least one illumination arrangement, wherein optical axes of each camera arrangement and optical axes of the at least one illumination arrangement are at least one of directed in different directions and substantially apart from each other in relation to the at least one eye and the device;
   wherein the one or more camera arrangements and the at least one illumination arrangement are configured for placement at least one of on the head of the object and to the front of the head of the object;
   wherein the device is configured to be switched into operating mode;
   a control arrangement that switches the camera arrangement to automatically take imaging of the at least one eye when the device is in the operating mode;
   wherein the control arrangement is configured to guide the camera arrangement and the at least one illumination arrangement;
   wherein at least one of the camera arrangement and the illumination arrangement can be moved relative to the other; and
   an image analyzing arrangement being configured to detect a reflection of the surface of the at least one eye that impedes the imaging in at least one of a picture taken by the camera arrangement and an image area of the camera arrangement, the image analyzing arrangement further being configured to transmit information corresponding to the reflection to the control arrangement, wherein the control arrangement is configured to at least one of repeat and discard the imaging based on the reflection.

2. The device according to claim 1, further comprising a support structure that, when the device is in the operating mode, contacts the skin around the at least one eye, wherein the support structure at least partly surrounds the at least one eye.

3. The device according to claim 1, further comprising a gaze guidance arrangement for guiding the at least one eye, wherein the control arrangement is provided to control the gaze guidance arrangement.

4. A device according to claim 1, further comprising an at least partly transparent part, wherein the device is configured such that the movements of the at least one eye can be guided through this at least partly transparent part by an external gaze guidance arrangement that is configured to be controlled by the control arrangement.

5. The device according to claim 1, further comprising a detector that is configured to detect when the device is in operation mode, when the device is in the front of the at least one eye, and when the at least one eye is in a predetermined position in relation to the camera arrangement.

6. The device according to claim 1, wherein the image analyzing arrangement is configured to detect deviations in at least one of the images and the image area and to transmit information corresponding to the deviations to the control arrangement, wherein the control arrangement is configured to at least one of repeat the imaging, provide a target, and mark the imaging in some way.

7. The device according to claim 1, wherein the control arrangement is configured to control at least one of the camera arrangement, illumination arrangement, and the gaze guidance arrangement when repeating the imaging.

8. The device according to claim 1, further comprising a motor arrangement being configured to move the camera arrangement.

9. The device according to claim 8, wherein the motor arrangement is configured to control the camera arrangement on x, y and z axes relative to the surface of the at least one eye and the pupil when the device is in operation mode in front of the at least one eye.

10. The device according to claim 8, wherein the motor arrangement is further configured to move the camera arrangement between imaging positions directed to different eyes.

11. The device according to claim 8, wherein the at least one eye comprises two eyes, wherein the at least one imaging arrangement comprises two imaging arrangements corresponding to the two eyes, respectively, the two imaging arrangements each comprising at least one camera arrangement and at least one motor arrangement.

12. The device according to claim 8, wherein the control arrangement is configured to activate the motor arrangement when the device is in operation mode and in the front of the at least one eye.

13. The device according to claim 1, wherein the control arrangement is configured to guide the camera arrangement to take the imaging based on at least one of imaging taken of the object previously and imaging collected from a large number of persons.

14. The device according to claim 1, wherein default values are saved in the control arrangement for selecting a point of imaging.

15. The device according to claim 1, further comprising a data transmission system configured to transmit at least the information corresponding to the reflection to an external service arrangement for at least one of storing and processing the information.

16. The device according to claim 15, wherein the data transmission system is configured to receive from the external service arrangement instructions for imaging that are at least one of characteristic to the object and that the service arrangement has calculated from the images of the object previously received; and wherein the data transmission system is configured to transmit the instructions to the control arrangement.

17. The device according to claim 1, wherein the device is configured to take imaging of one of part of the fundus and the surface of the at least one eye at a time.

18. The device according to claim 1, wherein the device is configured to take a measurement of at least one of shapes of the surface of the at least one eye and the reflection thereof, wherein the device makes an evaluation of the measurement of at least one of places of imaging and directions of imaging, wherein the control arrangement at least one of switches the camera arrangement and guides the camera arrangement to take imaging based on the evaluation.

19. The device according to claim 1, wherein the imaging is at least one of an image and a video.

20. A device for taking imaging of an eye having a surface, the device comprising:
- a camera arrangement being configured to take the imaging of the eye, wherein the camera arrangement has a first optical axis;
- an illumination arrangement being configured to direct light towards the eye, wherein the illumination arrangement has a second optical axis, wherein the first optical axis and the second optical axis are at least one of directed in different directions and substantially apart;
- a control arrangement being configured to move at least one of the camera and the illumination arrangement relative to the other; and
- an image analyzing arrangement being configured to detect a reflection of the surface of the eye in the imaging, the image analyzing arrangement being further configured to transmit information corresponding to the reflection to the control arrangement;
- wherein the control arrangement moves at least one of the camera arrangement and the illumination arrangement based on the information corresponding to reflection.

* * * * *